(12) United States Patent
Barlow et al.

(10) Patent No.: US 9,393,333 B2
(45) Date of Patent: Jul. 19, 2016

(54) DEVICES AND METHODS FOR EMANATING LIQUIDS (75) Inventors: Louise Margaret Barlow, Hull (GB); Ellen Piercy, Hull (GB); Steve Walsh, Camberley (GB)

(73) Assignee: RECKITT & COLMAN (OVERSEAS) LIMITED, Slough, Berkshire (GB)

( * ) Notice: Subject to any disclaimer, the term of this patent is extended or adjusted under 35 U.S.C. 154(b) by 1144 days.

(21) Appl. No.: 13/290,271

(22) Filed: Nov. 7, 2011

(65) Prior Publication Data

US 2012/0111966 A1 May 10, 2012

(30) Foreign Application Priority Data

Nov. 5, 2010 (GB) .................................. 1018697.1

(51) Int. Cl.
*A24F 25/00* (2006.01)
*A61L 9/04* (2006.01)
*A61L 9/03* (2006.01)
*A61L 9/12* (2006.01)
*A61L 9/14* (2006.01)

(52) U.S. Cl.
CPC ... *A61L 9/03* (2013.01); *A61L 9/12* (2013.01); *A61L 9/14* (2013.01); *A61L 2209/133* (2013.01)

(58) Field of Classification Search
CPC ............... A61L 9/03; A61L 9/14; A61L 9/12; A61L 2209/133
USPC .............. 239/6, 34, 44, 37, 41, 42, 43, 49, 45
See application file for complete search history.

(56) References Cited

U.S. PATENT DOCUMENTS

| 2,698,767 A | 1/1955 | Hartmann |
| 3,863,843 A | 2/1975 | Hechler, IV |
| 3,874,563 A | 4/1975 | Schwartzman |
| 4,200,229 A | 4/1980 | Spector |

(Continued)

FOREIGN PATENT DOCUMENTS

| EP | 0092359 A2 | 10/1983 |
| EP | 1076014 A2 | 2/2001 |

(Continued)

OTHER PUBLICATIONS

Notification Concerning Transmittal of International Preliminary Report on Patentability for PCT/GB2011/052151 dated May 16, 2013.

(Continued)

*Primary Examiner* — Len Tran
*Assistant Examiner* — Steven M Cernoch
(74) *Attorney, Agent, or Firm* — Norris McLaughlin & Marcus PA (57) ABSTRACT

The present invention describes a universal refill containing a volatile liquid adapted for use with at least two different types of emanation device; wherein the universal refill comprises a housing;
at least one reservoir in the housing for holding the volatile liquid; at least two valves in the housing in communication with the reservoir, wherein each of said valves is configured to be automatically resealable when not being held open; and wherein each type of device emanates the volatile liquid from the universal refill via a different mechanism to each other type of emanation device and wherein said at least two different types of emanation device each comprise a chassis configured to receive and releasably retain the universal refill.

32 Claims, 2 Drawing Sheets

(56) References Cited

U.S. PATENT DOCUMENTS

| | | | |
|---|---|---|---|
| 4,346,059 A | 8/1982 | Spector | |
| 4,582,807 A | 4/1986 | Veeraraghavan | |
| 4,852,807 A | 8/1989 | Stoody | |
| 4,921,071 A | 5/1990 | Lonnborg et al. | |
| 5,281,401 A | 1/1994 | Bryson | |
| 5,840,246 A | 11/1998 | Hammons et al. | |
| 6,050,025 A | 4/2000 | Wilbanks | |
| 6,170,717 B1 | 1/2001 | Giovanni et al. | |
| 6,308,867 B1 | 10/2001 | Wolter | |
| 6,622,662 B1 | 9/2003 | Wolpert et al. | |
| 7,249,719 B2 * | 7/2007 | He et al. | 239/44 |
| 7,377,493 B2 | 5/2008 | Thomas | |
| 2002/0168301 A1 | 11/2002 | Channer | |
| 2003/0005620 A1 | 1/2003 | Ananth et al. | |
| 2005/0155958 A1 | 7/2005 | Arai et al. | |
| 2005/0199742 A1 | 9/2005 | Maat | |
| 2006/0022064 A1 | 2/2006 | Triplett et al. | |
| 2006/0045359 A1 | 3/2006 | Chen et al. | |
| 2006/0110144 A1 | 5/2006 | Fellows et al. | |
| 2006/0118574 A1 | 6/2006 | Anderson et al. | |
| 2006/0175425 A1 | 8/2006 | McGee et al. | |
| 2007/0204387 A1 | 9/2007 | Cornelius et al. | |
| 2007/0217771 A1 | 9/2007 | Granger et al. | |
| 2008/0087737 A1 | 4/2008 | Dunne et al. | |
| 2008/0149665 A1 | 6/2008 | Hafer et al. | |
| 2008/0251598 A1 | 10/2008 | Ross | |
| 2009/0184175 A1 | 7/2009 | Blankenstein et al. | |
| 2009/0220222 A1 | 9/2009 | Rabin et al. | |
| 2010/0243754 A1 | 9/2010 | Harris | |
| 2012/0168971 A1 | 7/2012 | Hansen et al. | |
| 2012/0237404 A1 | 9/2012 | Woolley | |

FOREIGN PATENT DOCUMENTS

| | | |
|---|---|---|
| EP | 1714662 A1 | 10/2006 |
| EP | 1849485 A1 | 10/2007 |
| FR | 2556242 A1 | 6/1985 |
| GB | 2233230 A | 1/1991 |
| GB | 2357973 A | 7/2001 |
| GB | 2480906 A | 12/2011 |
| JP | 2005224464 A | 8/2005 |
| WO | 9949904 A1 | 10/1999 |
| WO | 03003826 A3 | 1/2003 |
| WO | 03103387 A3 | 12/2003 |
| WO | 2004002542 A1 | 1/2004 |
| WO | 2006004891 A1 | 1/2006 |
| WO | 2006045359 A1 | 5/2006 |
| WO | 2007109504 A2 | 9/2007 |
| WO | 2008034977 A2 | 3/2008 |
| WO | 2008049852 A1 | 5/2008 |
| WO | 2008149066 A1 | 12/2008 |
| WO | 2009044123 A1 | 4/2009 |
| WO | 2012001405 A1 | 1/2012 |
| WO | 2012059771 A1 | 5/2012 |

OTHER PUBLICATIONS

International Preliminary Report on Patentability for PCT/GB2011/052151 dated May 7, 2013.
Written Opinion of the International Searching Authority for PCT/GB2011/052151 dated Jan. 13, 2012.
International Search Report for PCT/GB2011/052151 dated Jan. 13, 2012.
Combined Search and Examination Report under Sections 17 and 18(3) for application GB 1018697.1 dated Mar. 7, 2011.

* cited by examiner

DEVICES AND METHODS FOR EMANATING LIQUIDS

This is an application filed under 35 USC 119 of UK Patent Appn. 1018697.1 filed 5 Nov. 2010.

FIELD OF THE INVENTION

The present invention relates to devices and methods for improved airborne delivery of volatile liquids containing one or more active materials wherein the active material comprises at least one of: a fragrance; an insecticide; a fungicide; a pesticide; a sanitising material; and/or a pharmaceutical.

BACKGROUND

Volatile liquids containing one or more active materials wherein the active material comprises at least one of a fragrance; an insecticide; a fungicide; a pesticide; a sanitising material; and/or a pharmaceutical are delivered within the domestic environment via a variety of mechanisms. Devices are available with heaters disposed therein to increase the rate of emanation from a surface saturated with the liquid, such a surface could be a wick saturated with a fragranced liquid and the heater is located adjacent the wick surface and nearby a chimney to heat the liquid on the wick surface and cause it to more readily evaporate and disseminate into the surrounding environment through the chimney.

Alternatively such volatile liquids can be loaded into an aerosol canister wherein the canister holds the liquid under pressure and when a valve is opened the liquid is forced out. The liquid is provided with a propellant which evaporates inside the canister to maintain an even pressure and, outside the canister, assist with the mechanical break up of the liquid by evaporating rapidly. Suitable propellants include volatile hydrocarbons such as propane, butane or isobutane.

Aerosols generally provide a satisfactory spray performance but since they require manual operation by a user, they are not considered to be particularly convenient for routine use.

Automatic aerosol activation devices exist for operation with metered dose aerosols containing a single phase volatile liquid and propellant mixture. These devices are operable to periodically actuate the aerosol to cause a dose of the liquid to be sprayed.

Whilst the automation of the aerosol spraying devices overcomes the problem of manual operation of an aerosol canister, the use of aerosols containing such propellants is becoming increasingly less desirable since these volatile hydrocarbons carry the disadvantage of being flammable, the rising cost of oil is rendering them increasingly expensive and they also carry the further disadvantage of being an atmospheric source of carbon which is deemed to not be environmentally sensitive.

There are other known emanation devices using alternative emanation methodologies such as nebulisation techniques using a piezo-actuated apparatus for instance.

All of the known emanation devices and methodologies of emanation possess advantages and disadvantages with respect to each other that will be appreciated by a person skilled in the art as well as the ultimate consumer. However, invariably the consumer is faced with a dilemma when purchasing any particular emanation device as the emanation method employed by the emanation device under consideration is not the only factor the consumer must also consider, the consumer must also consider the availability and range of refills of volatile liquids to be used with said device. In the field of air freshening in particular where the range of fragrances the consumer can select for use with the device is a key point of purchase consideration for the consumer, a small range of fragrances and/or fear that the refill range may not be supported in the long term may affect the consumer's true freedom of choice. The present invention addresses this and other problems.

SUMMARY OF INVENTION

According a first aspect of the present invention there is provided therefore a universal refill of volatile liquid containing one or more active materials wherein the refill comprises:
a housing;
at least one reservoir in the housing for holding the volatile liquid;
at least two valves in the housing in communication with the reservoir, wherein each of said valves is configured to be automatically resealable when not being held open;
and wherein the refill is configured to allow the volatile liquid to be extracted by at least two different method of liquid extraction.

According a second aspect of the present invention there is provided therefore a universal refill containing a volatile liquid for use with at least two different types of emanation device;
wherein the universal refill comprises
a housing;
at least one reservoir in the housing for holding the volatile liquid;
at least two valves in the housing in communication with the reservoir, wherein each of said valves is configured to be automatically resealable when not being held open;
and wherein each type of device emanates the volatile liquid from the universal refill via a different mechanism to each other type of emanation device and wherein said at least two different types of emanation device each comprise a chassis configured to receive and releasably retain the universal refill and wherein each device further comprises one or more liquid extraction means which are configured to extend from the device and, in use, through one or more of said valves of the universal refill.

According to a third aspect of the present invention there is provided a liquid dispensing system comprising a universal refill of volatile liquid and an emanation device; wherein the refill comprises:
a housing;
at least one reservoir in the housing for holding the volatile liquid;
at least two valves in the housing in communication with the reservoir, wherein each of said valves is configured to be automatically resealable when not being held open;
wherein the refill is operationally compatible with each device;
and wherein the emanation device is selected from at least one of; an emanation device configured to spray the volatile liquid; an emanation device configured to evaporate the volatile liquid by electrically powered means; an emanation device configured to evaporate the volatile liquid by passive, non-electrically powered means; an emanation device configured to emanate the volatile liquid by two or more of spraying the volatile liquid, evaporating the volatile liquid by electrically powered means and/or evaporating the volatile liquid by passive, non-electrically powered means;
characterised in that each emanation device is provided with a chassis configured to receive and releasably retain the universal refill and wherein each device further comprises one or more liquid extraction means which are configured to extend from the device and, in use, through one or more of said valves of the universal refill.

According to a fourth aspect of the present invention there is provided a liquid dispensing system comprising a universal refill of volatile liquid and an emanation device; wherein the refill comprises:

a housing;

at least one reservoir in the housing for holding the volatile liquid;

at least two valves in the housing in communication with the reservoir, wherein each of said valves is configured to be automatically resealable when not being held open;

wherein the refill is operationally compatible with each device;

and wherein the emanation device is selected from at least one of: an emanation device configured to extract the volatile liquid from the refill by pumping the liquid therefrom; an emanation device configured to extract the volatile liquid from the refill by blowing the liquid therefrom; an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom;

characterised in that each emanation device is provided with a chassis configured to receive and releasably retain the universal refill and wherein each device further comprises one or more liquid extraction means which are configured to extend from the device and, in use, through one or more of said valves of the universal refill.

According to a fifth aspect of the present invention there is provided a liquid dispensing device for use with a universal refill of volatile liquid and an emanation device; wherein the refill comprises:

a housing;

at least one reservoir in the housing for holding the volatile liquid;

at least two valves in the housing in communication with the reservoir, wherein each of said valves is configured to be automatically resealable when not being held open;

wherein the refill is operationally compatible with each device;

wherein the emanation device is selected from: an emanation device configured to extract the volatile liquid from the refill by pumping the liquid therefrom; an emanation device configured to extract the volatile liquid from the refill by blowing the liquid therefrom; an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom;

characterised in that each emanation device is provided with a chassis configured to receive and releasably retain the universal refill and wherein each device further comprises one or more liquid extraction means which are configured to extend from the device and, in use, through one or more of said valves of the universal refill.

In the context of the present invention the term "operationally compatible" in reference to the universal refill is understood as meaning that said refill is capable, in use, of cooperating with the emanation device to release the volatile liquid from the refill to the device for emanation into the environment surrounding the device.

Preferably the universal refill is provided with securing means which are configured, in use, to cooperate with the chassis and/or the emanation device to permit secure engagement therewith. Preferably the securing means form a part of the external surface of the housing.

At least one of the valve(s) may be provided by a flexible material possessing resilient properties which causes the valve(s) to adopt a closed position when not being held open. Suitable flexible resilient material for the valve(s) may include at least one of silicon and silicon derivatives; EPDM; EVA; EPDM/PP copolymer; PVC; thermoplastic rubber; butadiene/acrylonitrile; perfluoroelastomer; fluorosilicon; ETPV; thermoplastic; polyester elastomer; PA elastomer; TPE.

Alternatively or additionally at least one of the valve(s) may be provided by a sealing means biased into a closed position by a deformable biasing means such as a spring means or the like.

The at least two valves are preferably provided substantially adjacent to each other. The housing of the refill preferably comprises six sides, namely, a front side, rear side, top side, bottom side, and right and left sides and the at least two valves are preferably provided on the same side of the refill housing.

The at least two valves may not be identical, for instance, one of said valves could be a self-sealing flexible resilient valve and the another of said valves could be a sealing means biased into a closed position by a deformable biasing means such as a spring means or the like.

One or more of said at least two valves could be adjustable to affect the flow rate of the volatile liquid therethrough. The adjustability may be facilitated manually by a user and/or due to an automated function of the emanation device, said automated function may be controlled automatically by the emanation device or may be in response to a user input into the device. Adjustability may be particularly useful when the emanation device is configured to emanate the volatile liquid passively and/or extract the liquid passively such as by gravity feed.

The valves may be configured to be operable such that when the universal refill is engaged with the chassis of an emanation device the liquid extraction means which extend, in use, into the refill are sealed against to substantially prevent any leaking of the volatile liquid between the valve and the extraction means. Alternatively or additionally, the valves may be provided with additional sealing means adjacent thereto, such as an o-ring or the like, wherein said additional sealing means are operable such that when the universal refill is engaged with the chassis of an emanation device any liquid extraction means from the device which protrude into the refill are sealed against by the additional sealing means to substantially prevent any leaking of the volatile liquid between the valve and the extraction means. It may be advantageous for the universal refill for the valves to be configured to seal against the extract means of an emanation device together with the refill being provided with additional sealing means in order to provide redundancy in sealing when the refill is engaged with the chassis of an emanation device.

The liquid extraction means may be provided in several different forms depending on the emanation device in question and the type of extraction/emanation technique to be deployed. For example the liquid extraction means for each emanation device may comprise one or more of: a liquid conduit; a liquid wicking conduit; a wick; a liquid capillary; an air conduit for venting; a blown air conduit; combinations of same; and the like.

The universal refill is preferably formed with a housing of rigid or substantially rigid material. Such an arrangement may be advantageous as differing forms of extraction of volatile liquid therefrom may put different strains and pressures on the refill and by providing the housing of the refill in a rigid or substantially rigid material, the refill may be better able to resist those differing strains and pressures to deliver uniform and/or predictable characteristics.

The refill housing is preferably shaped such that a user may only may able to engage the refill with a chassis in a single orientation. For instance, if the refill was generally cylindrical with the valves being provided on the circular end of the cylinder, a user could load the circular end into the chassis in various orientations which may prevent ease of engagement of the refill therein, whereas if the face of the refill containing the valves was, for instance, rhomboidal then the user would be presented with only a single option for orienting the refill in the chassis.

Alternatively, the refill housing may be shaped such that a user may ostensibly be presented with more than one orientation in which they could engage the refill with a chassis and in this arrangement the chassis is preferably provided with guide means which cooperate with features of the refill housing to ensure that the refill can only be engaged with the chassis in a single orientation such that efforts by the user to incorrectly load the refill in the chassis will be resisted thereby.

The universal refill is preferably provided with one reservoir which is accessible from both of said at least two valves.

Preferably the universal refill is provided with one or more diptubes therein. Preferably the or each diptube is provided adjacent the valve(s) such that, in use, the liquid extraction means of the emanation device may be configured to be in liquid communication therewith when the refill is engaged with said device. Most preferably the universal refill is provided with a single diptube adjacent one of the valves. The presence of a diptube may be advantageous as this may better optimise the ability of the universal refill to operate in a number of different orientations when engaged with the chassis of an emanation device. Preferably a single diptube is provided within the refill and is located adjacent one of said at least two valves such that, in use, the extraction means from an emanation device can cooperate therewith on entering the valve and, most preferably said extraction means are configured to engage with the diptube to facilitate said cooperation therewith. Alternatively a single diptube is provided within the refill and is located integral with one of said at least two valves such that, in use, the extraction means from an emanation device can cooperate therewith on entering the valve and, most preferably said extraction means are configured to engage with the diptube to facilitate said cooperation therewith.

The reservoir(s) may be provided in the form of flexible bags which are capable of collapsing inwardly as volatile liquid is extracted therefrom.

The refill may be provided with one or more vent holes in the refill housing which are formed to permit air to enter the reservoir(s) when volatile liquid is removed therefrom but not to permit the volatile liquid to escape therethrough. The vent hole(s) may be covered with a gas permeable membrane. Alternatively the vent hole(s) may be covered with an automatically resealable means which engages with a seal opening means of the chassis. Preferably however, the vent hole(s) are preferably sized such that the volatile liquid may not escape therefrom or that the rate of escape would be sufficiently low as to not be relevant for the safe operation of the refill in an emanation device.

The refill housing is preferably provided have a section thereof adjacent the reservoir(s) that is substantially transparent to permit a user to easily determine what type of volatile liquid is held therein and/or the level of said volatile liquid.

The chassis may be formed as a separate component to the emanation device and may be mounted on or in the device to receive and releasably retain the universal refill. Alternatively or additionally, the chassis may be formed in an exterior surface of the emanation device (such as a device housing). Alternatively or additionally the chassis may be formed within the interior of the device and a suitably shaped aperture is provided to permit access to the interior of the housing by the universal refill. Alternatively or additionally the chassis may be formed within the interior of the device and the device is provided with a door which may be opened to permit access to the interior of the housing by the universal refill.

Where the emanation device is to pump the volatile liquid from the reservoir(s) of the universal refill the extraction means of the emanation device may be provided with one or more liquid conduits that are connected at one end to a pumping means housed within the device and open at the other end to be in liquid communication with the volatile liquid. Preferably for a refill with two valves a single liquid conduit is provided and a single air conduit for venting is provided. In this arrangement the liquid conduit is preferably sized to extend through one of the valves in the universal refill and the air conduit for venting extends though the other valve such that both conduits extend into the reservoir(s) therewithin when the refill is engaged with the chassis. In use the pump may be operable via conventional pumping mechanisms to create negative pressure within the liquid conduit(s) in order to draw the volatile liquid into the conduit(s) and transport same toward the pump, whilst the air conduit for venting allows air to enter the refill to prevent an over pressurisation of the refill and/or to allow air to re-enter the refill once the pumping is complete. Once the volatile liquid is in the device it may be emanated therefrom in any of a number of convention mechanisms, non-limiting examples include: the pumped liquid may be transported to an open emanation plate in combination with a heater to promote evaporation of the liquid; or the liquid may be transported to a nebuliser and it is atomised thereby; etc.

Where the emanation device is to blow the volatile liquid from the reservoir(s) of the universal refill the extraction means of the emanation device of the emanation device may be provided with one or more blown air conduits that are connected at one end to a blowing means housed within the device and open at the other end to permit blown air to exit therefrom and with one or more liquid conduits that are open at one end to be in liquid communication with the volatile liquid in the reservoir and connected to the device at the other end. Preferably for a refill with two valves a single liquid conduit is provided and a single blown air conduit is provided. In this arrangement the liquid conduit is preferably sized to extend through one of the valves in the universal refill and the blown air conduit extends though the other valve such that both conduits extend into the reservoir(s) therewithin when the refill is engaged with the chassis. In use, the blowing means may be operable to blow air along the blown air conduit and into the reservoir(s) in order to pressurise the head space (i.e.—the head space is the space within the reservoir(s) not taken up by the volatile liquid) and, when required by the device, force liquid into the liquid conduit(s) and toward the device. Volatile liquid transported along the liquid conduit(s) may be emanated therefrom in any of a number of convention mechanisms, non-limiting examples include: the liquid may be sprayed directly from the device under the force of said transportation and/or in combination with additional blown air from the blowing means; or the liquid may be transported to a nebuliser and for it to be atomised thereby; etc.

Where the emanation device is to wick the volatile liquid from the reservoir(s) of the universal refill the emanation device may be provided with one or more wicks that are connected at one end to the emanation device and configured at the other end to be in liquid communication with the volatile liquid to uptake same via wicking action. The wick(s) are preferably sized to extend through one or more of the valves in the universal refill and into the reservoir(s) therewithin when the refill is engaged with the chassis. In use, the wick(s) may be operable to passively uptake liquid from the reservoir(s) and transport same towards the other end of the wick(s). Once the volatile liquid is within the wick(s) it may be emanated from the device in any of a number of convention mechanisms; non-limiting examples include: the liquid may be emanated directly from the wick(s) passively and/or in combination with powered means to assist in the evaporation such as an electrically powered heater; or the liquid may be transported to along the wick(s) to a nebuliser and it is atomised thereby; etc.

Where the emanation device is to transport the volatile liquid from the reservoir(s) of the universal refill to the emanation device via capillary action the device may be provided with one or more capillary tubes that are connected at one end to the emanation device and configured at the other end to be in liquid communication with the volatile liquid to uptake same via capillary action. The capillary tube(s) are preferably sized to extend through one or more of the valves in the universal refill and into the reservoir(s) therewithin when the refill is engaged with the chassis. In use, the capillary tube (s) may be operable to passively uptake liquid from the reservoir(s) and transport same towards the other end of the tube(s). Volatile liquid transported along the capillary tube(s) to the emanation device may then be emanated therefrom in any of a number of convention mechanisms, non-limiting examples include: the liquid may be transported to an open emanation plate in combination with a heater to promote evaporation of the liquid; or the liquid may be transported to a nebuliser and it is atomised thereby; etc.

Where the emanation device is to extract the volatile liquid from the reservoir(s) of the universal refill toward the emanation device by a gravity feed mechanism the emanation device may be provided with one or more liquid conduits that are connected at one end to the device and open at the other end to be in liquid communication with the volatile liquid. The liquid conduit(s) are preferably sized to extend through one or more of the valves in the universal refill and into the reservoir(s) therewithin when the refill is engaged with the chassis. The chassis is orientated such when the universal refill is engaged therewith the valves of the refill are located closer to a supporting surface on which the device is held such that once the valve(s) are opened by the liquid conduit(s) the force of gravity will cause liquid to travel from the refill toward the device. In use, the liquid conduit(s) may be operable to simply open the valve(s) to permit the volatile liquid to flow from the reservoir toward the device to emanate the liquid by any of a number of convention emanation mechanisms, non-limiting examples include: the liquid flow into an open emanation plate in combination with a heater to promote evaporation of the liquid; or the liquid may flow toward a nebuliser for it to be atomised thereby; etc.

The emanation device and/or chassis may be provided with securing means which are configured to engage with the universal refill to permit a secure engagement of the universal refill to the chassis. Preferably the releasable engagement between the universal refill and the chassis is provided with a positive feedback for the user; such as a "push-click" mechanism wherein the user pushes the refill against the chassis until an audible "click" sound is achieved and the refill is secured relative to the chassis, and to disengage the universal refill from the chassis the user pushes the refill against the chassis until a further "click" sound is achieved accompanied by a physical sensation of the refill being pushed away from the chassis and the user may separate the refill from the device.

The universal refill and emanation devices are preferably provided with a device-to-refill recognition system whereby the device is able to recognise the level of volatile liquid remaining in the refill and/or the type of volatile liquid in the refill and/or whether the refill is from a known source. The recognition system may be provided by the device possessing a physical characteristic in the refill housing which interacts with a portion of the chassis and/or device. The recognition system may comprise a moulded feature in the reservoir(s) which may have a communication component embedded therein which can communicate with a corresponding communication component within the device and/or the moulded feature may act as a convenient means to for the device to make reference against when determining the level of volatile liquid in the reservoir(s). The recognition system may be provided with an identification means being applied to and/or within the refill housing such as a visual code, an RUM tag, printed electrical components, magnets or the like. The recognition system may be provided by any combination of the aforesaid recognition systems.

According to a sixth aspect of the present invention there is provided a method of dispensing a volatile liquid from a universal refill, wherein the refill comprises: a housing; at least one reservoir in the housing for holding the volatile liquid; at least two valves in the housing in communication with the reservoir, wherein each of said valves is configured to be automatically resealable when not being held open; and wherein the emanation device is selected from at least one of: an emanation device configured to extract the volatile liquid from the refill by pumping the liquid therefrom; an emanation device configured to extract the volatile liquid from the refill by blowing the liquid therefrom; an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom; wherein each emanation device is provided with a chassis configured to receive and releasably retain the universal refill and wherein each emanation device further comprises one or more liquid extraction means; and wherein the method comprises the steps of:
connecting a universal refill to the chassis of a first emanation device configured to extract the volatile liquid via a first extraction mechanism such that the extraction means enters the valve(s) of the universal refill;

operating the emanation device such that volatile liquid moves from the refill to the device and said liquid is emanated into the surrounding environment by the device; disconnecting the universal refill;
connecting a universal refill to the chassis of a second emanation device configured to extract the volatile liquid via a second extraction mechanism such that the extraction means enters the valve(s) of the universal refill;
operating the emanation device such that volatile liquid moves from the refill to the device and said liquid is emanated into the surrounding environment by the device;
wherein the first emanation device and first extraction mechanism is different from the second emanation device and second extraction mechanism.

According to a seventh aspect of the present invention there is provided a method of dispensing a volatile liquid from a universal refill, wherein the refill comprises: a housing; at least one reservoir in the housing for holding the volatile liquid; at least two valves in the housing in communication with the reservoir, wherein each of said valves is configured to be automatically resealable when not being held open;
and wherein the emanation device is selected from at least one of; an emanation device configured to emanate the volatile liquid by spraying said volatile liquid; an emanation device configured to emanate the volatile liquid by evaporating the volatile liquid by electrically powered means; an emanation device configured to emanate the volatile liquid by evaporating the volatile liquid by passive, non-electrically powered means; an emanation device configured to emanate the volatile liquid by two or more of spraying the volatile liquid, evaporating the volatile liquid by electrically powered means and/or evaporating the volatile liquid by passive, non-electrically powered means; wherein each emanation device is provided with a chassis configured to receive and releasably retain the universal refill and wherein each emanation device further comprises one or more liquid extraction means; and wherein the method comprises the steps of:
connecting a universal refill to the chassis of a first emanation device configured to emanate the volatile liquid via a first emanation mechanism such that the extraction means enters the valve(s) of the universal refill;
operating the emanation device such that volatile liquid moves from the refill to the device and said liquid is emanated into the surrounding environment by the device; disconnecting the universal refill;
connecting a universal refill to the chassis of a second emanation device configured to emanate the volatile liquid via a second emanation mechanism such that the extraction means enters the valve(s) of the universal refill;
operating the emanation device such that volatile liquid moves from the refill to the device and said liquid is emanated into the surrounding environment by the device;
wherein the first emanation device and first emanation mechanism is different from the second emanation device and second emanation mechanism.

Any of the features described herein may be combined with any of the above aspects in any combination.

BRIEF DESCRIPTION OF THE DRAWINGS

Embodiments of the invention will now be described, by way of example only, with reference to the following drawings in which.

DESCRIPTION OF AN EMBODIMENT

Figure 1:
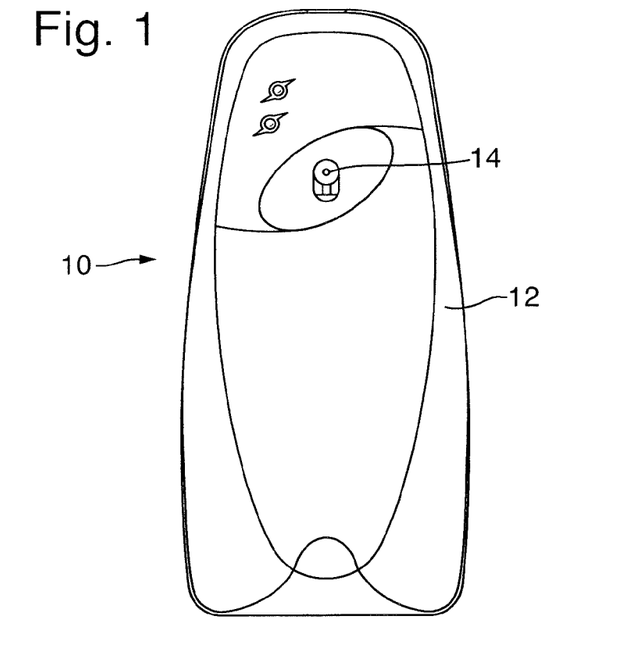
FIG. 1 illustrates a prior art automatic aerosol emanation device.

FIG. 1 illustrates a well known battery-operated automatic aerosol emanation device (10). The device (10) comprises a housing 12 which supports a platform (not shown) in the interior of the device (10). The platform, in turn, supports and retains an aerosol canister of pressurised fluid (not shown), specifically, air freshening fluid comprising various components including fragrance, solvent and propellant. The housing 12 also supports an actuation means (not shown), which is sprayed from the aerosol canister by an arm of the actuation mean bearing against a spray head (14) of the aerosol canister to move it in a generally downward direction until the spray head is depressed and the valve within the aerosol is opened, thus, causing a quantity of fluid to be sprayed therefrom. For this sort of arrangement it would be preferable for the aerosol canister to contain a single phase formulation so that the aerosol can be of a metered dose arrangement.

Alternatively, although not shown the prior art device (10) could be provided with actuation means which take the form of a valve system, such as a solenoid valve system. In such an arrangement the aerosol canister would be provided without a spray head, rather the valve stem of the aerosol canister would engage directly with the solenoid valve system of the device. In this arrangement rather than the actuation means initiating actuation by movement of an arm, the solenoid valve would be energised to initiate the release of a quantity of fluid from the aerosol.

For these two well known types of prior art devices that work in ostensibly the same way, by spraying, ostensibly with the same refill, a single phase aerosol formulation provided in an aerosol canister, they require different refills which poses a series of dilemmas to the end consumer/user, such dilemmas include availability of refills, the range of refills, the value perception/consumer benefit of one particular device and refill range versus a different device and refill, etc. Similar dilemmas face the retailer, how much shelf space can they allot to one range of devices and refills, does the amount of shelf space necessarily limit the different varieties of that specific refill they can retail which in turn affects the end consumer/user's decision to purchase and re-purchase, etc.

Figure 2:
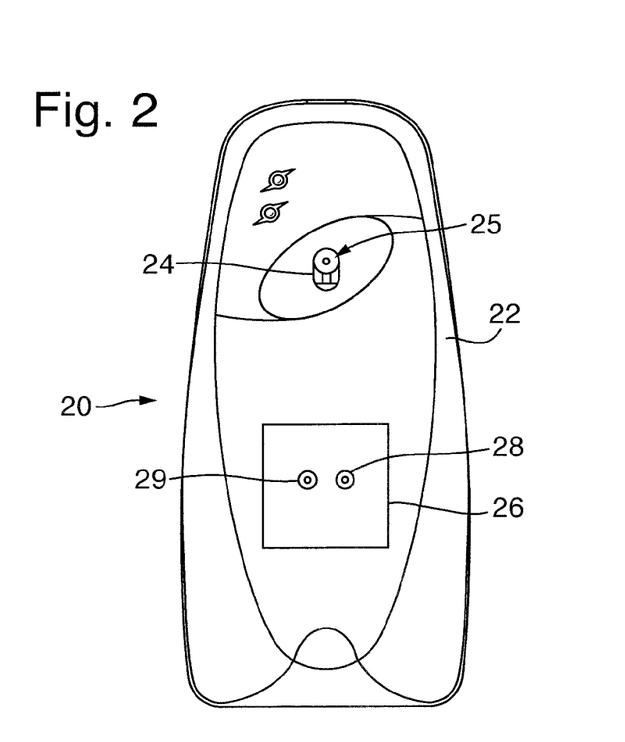
FIG. 2 illustrates a spraying emanation device suitable for use with a universal refill according to the present invention.

FIG. 2 shows an emanation device (20) of the present invention which has a similar general appearance to a known prior art device (10) but differs in several important details. The emanation device (20) has a housing (22) and an aperture (24) through which, in use, liquid may be emanated. However, the device (20) has a chassis (26) formed integrally with a front face of the housing (22) to provide a recess of suitable dimensions to receive a universal refill (30). The chassis (26) is provided with two liquid extraction means in the form of conduits (28,29) which protrude from within the interior of the chassis (26). Each of these conduits (28,29) is operatively connected to emanation means (not shown) within the device (20) and this will be discussed in greater detail below.

Figure 3:
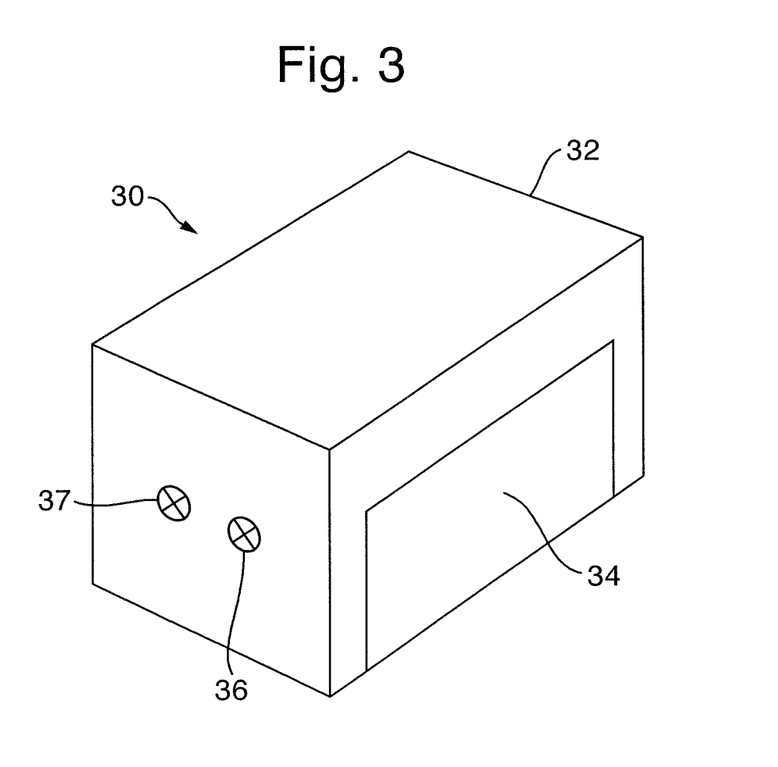
FIG. 3 illustrates a universal refill according to the present invention.

FIG. 3 shows a universal refill (30). The refill (30) comprises a housing (32) which is made, preferably, of a rigid material such as a hardened plastics material or the like. The housing has a viewing window (34) to the reservoir of the refill (30) which allows a visual check on the level of volatile liquid held therein. Two automatically resealable valves (36, 37) are provided in one end of the housing. In this embodiment the both of the valves (36,37) are provided by self-sealing silicone valves. Although not shown, a diptube is associated with one of the valves (36) such that it is adjacent to or formed with the valve (36) to be substantially integral therewith.

A dispensing system of the present invention is created by a user locating the refill (30) such that the end of the refill containing the valves (36,37) is facing the chassis (26) of the device (20). The user then pushes the refill (30) into the chassis (26) and by doing so forces the two conduits (28,29) into the valves (36,37) opening them. The user continues to push the refill (30) into the chassis (26) until the refill is secured against securing means (not shown), a user would understand when the securing means had been engaged due to positive feedback being received in the form of an audible click.

The end of the housing containing the two valves (36,37) is substantially square in shape and guide means in the chassis in the form of protruding notches (not shown) would cooperate with grooves in the refill housing (not shown) to ensure that the refill could only be engaged with the chassis if conduit (28) opens valve (37) and that the other conduit (29) opens the other valve (36) to cooperate with the diptube and, preferably, to engage with the diptube to cooperate therewith. Although not illustrated, the end of the refill housing containing the valves (36,37) could be shaped such that the loading thereof into the chassis (26) was only possible via a single orientation of that end of the refill.

Emanation device (20) is arranged to spray the volatile liquid out of the aperture (24) and it does this by blowing liquid from the refill (30). Specifically, one of the conduits (28) is arranged to blow air into the refill (30) and the other conduit (29) is arranged to extract liquid from the refill (30) via the diptube. In use, an air pump (not shown) in the device (20) blows air along the conduit (28) and into the reservoir of the refill (30) in order to pressurise the head space (i.e.—the head space is the space within the reservoir(s) not taken up by the volatile liquid), this increase in internal pressure forces the volatile liquid into the diptube and from there into the other conduit (29) through which the liquid is transported into the device (20). Once the liquid is in the device the force of the transportation from the refill in combination with additional blown air from the air pump causes the liquid to be forced toward a spray nozzle (25) which consists of a series of perforations which assist in the mechanical break up of the volatile liquid as it passes therethrough to result in a fine spray of particles of volatile liquid.

After a period of spraying of the volatile liquid from the refill (30) by the emanation device (20), the user may remove the refill (30) from the chassis (26). The user does this by pushing the refill against the positive feedback mechanism of the securing means until an audible click is heard again by the user which signifies the release by the securing means of the refill thus permitting the refill (30) to be freely removable from the chassis (26) by the user.

The user is then able to re-use refill (30) is a different second emanation device (not shown) which extracts and/or emanates the volatile liquid via a different mechanism to that of spraying emanation device (20), this may be beneficial if the different device is located in a different location where the user wishes to create a different atmosphere. For instance, where the volatile liquid is an air freshener, the spraying emanation device (20) may be located in the kitchen of a user's home for the instantaneous targeting of cooking smells as required by the user, whereas in the lounge of the user's home, the user would prefer to create a background ambience of fragrance rather than target unwanted odours. In this proposed situation, a user may take partially used refill (30) and load it into the chassis of a different emanation device (not shown) which extracts the liquid from the refill (30) passively.

The different emanation device may have the same appearance as spraying emanation device (20), however, the extraction means of the emanation device would possess a rigid outer surface and an inner core of porous material. As the user engages the refill (30) with the extraction means the rigid outer surface thereof opens the valve (36,37) thus allowing the volatile liquid to contact the inner porous core. The core of the extraction means is then able to passively wick the liquid into the device toward an emanation substrate of porous material adjacent a heater mounted in the device. The heater is operable to gently heat the emanation substrate to promote the evaporation of the volatile liquid therefrom to create a constant and slow emanation of the atomised liquid into the surrounding environment.

Thereafter a user may elect to remove the refill (30) from the second emanation device and use it in a third emanation device (not shown), perhaps located adjacent a toilet, wherein the third emanation device is operable in use to pump the volatile liquid from the universal refill (30) to transport the liquid to a nebuliser which operable to atomised the liquid into the surrounding environment.

Thereafter a user may elect to remove the refill (30) from the third emanation device and use it in a fourth emanation device (not shown), perhaps located in a bedroom, wherein the fourth emanation device is operable in use to use capillary action to transport the volatile liquid from the universal refill (30) to an open plate in the device such that a user can watch the liquid slowly and methodically drop into the open plate from where the liquid can evaporate into the surrounding environment.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A liquid dispensing system comprising a universal refill of volatile liquid and an emanation device; wherein the refill comprises:
   a housing;
   at least one reservoir in the housing for holding the volatile liquid;
   at least two valves in the housing in communication with the reservoir, wherein each of said valves is configured to be automatically resealable when not being held open;
   wherein the refill is operationally compatible with each device;
   wherein the emanation device is selected from at least one of: an emanation device configured to extract the volatile liquid from the refill by pumping the liquid therefrom;

an emanation device configured to extract the volatile liquid from the refill by blowing the liquid therefrom; an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom wherein each emanation device is provided with a chassis configured to receive and releasably retain the universal refill and wherein each device further comprises one or more liquid extraction means which are configured to extend from the device and, in use, through one or more of said valves of the universal refill, wherein when the emanation device, in use, wicks the volatile liquid from the reservoir(s) of the universal refill the extraction means of the emanation device is provided by one or more wicks that are connected at one end to the emanation device and configured at the other end to be in liquid communication with the volatile liquid and uptake same, and further wherein the wick(s) are sized to extend through one or more of the valves in the universal refill and into the reservoir(s) therewithin when the refill is engaged with the chassis.

2. A liquid dispensing system according to claim 1, wherein the universal refill is provided with securing means which are configured, in use, to cooperate with the chassis and/or the emanation device to permit secure engagement therewith.

3. A liquid dispensing system according to claim 1, wherein at least one of the valves is provided by a flexible material possessing resilient properties which causes the valve (s) to adopt a closed position when not being held open.

4. A liquid dispensing system according to claim 1, wherein at least one of the valve(s) is provided by a sealing means biased into a closed position by a deformable biasing means.

5. A liquid dispensing system according to claim 1, wherein the at least two valves are provided substantially adjacent to each other on the same side of the refill housing.

6. A liquid dispensing system according to claim 1, wherein the valves are configured to be operable such that when the universal refill is engaged with the chassis of an emanation device the liquid extraction means from the device which protrude into the refill are sealed against to substantially prevent any leaking of the volatile liquid between the valve and the extraction means.

7. A liquid dispensing system according to claim 1, wherein the valves are provided with additional sealing means adjacent thereto, wherein said additional sealing means are operable such that when the universal refill is engaged with the chassis of an emanation device any liquid extraction means from the device which protrude into the refill are sealed against by the additional sealing means to substantially prevent any leaking of the volatile liquid between the valve and the extraction means.

8. A liquid dispensing system according to claim 1, wherein the universal refill is provided with one or more diptubes therein.

9. A liquid dispensing system according to claim 8, wherein the or each diptube is provided adjacent the valve(s) such that, in use, the liquid extraction means of the emanation device is configured to be in liquid communication therewith when the refill is engaged with said device.

10. A liquid dispensing system according to claim 8, wherein the universal refill is provided with a single diptube adjacent one of the valves.

11. A liquid dispensing system according to claim 8, wherein the single diptube is provided adjacent one of said at least two valves such that, in use, the extraction means from an emanation device is configured to engage with the diptube to facilitate cooperation therewith.

12. A liquid dispensing system according to claim 8, wherein the single diptube is integral with one of said at least two valves such that, in use, the extraction means from an emanation device is configured to engage with the diptube to facilitate said cooperation therewith.

13. A liquid dispensing system according to claim 12, wherein the universal refill is formed with a housing of rigid or substantially rigid material.

14. A liquid dispensing system according to claim 12, wherein the refill housing is shaped such that a user may only may able to engage the refill with a chassis in a single orientation.

15. A liquid dispensing system according to claim 12, wherein the chassis is formed as a separate component to the emanation device and is mounted on or in the device to receive and releasably retain the universal refill.

16. A liquid dispensing system according to claim 12, wherein the chassis is formed in an exterior surface of the emanation device.

17. A liquid dispensing system according to claim 12, wherein the chassis is formed within the interior of the device and a suitably shaped aperture is provided to permit access to the interior of the housing by the universal refill.

18. A liquid dispensing system according to claim 12, wherein the chassis is formed within the interior of the device and the device is provided with a door to permit access to the interior of the housing by the universal refill.

19. A liquid dispensing system according to claim 12, wherein when the emanation device, in use, pumps the volatile liquid from the reservoir(s) of the universal refill, the extraction means of the emanation device is provided by one or more liquid conduits that are connected at one end to a pumping means housed within the device and open at the other end to be in liquid communication with the volatile liquid.

20. A liquid dispensing system according to claim 19, wherein the liquid conduit(s) are sized to extend through one or more of the valves in the universal refill and into the reservoir(s) therewithin when the refill is engaged with the chassis.

21. A liquid dispensing system according to claim 19, wherein, in use, the pump is operable to create negative pressure within the liquid conduit(s) in order to draw the volatile liquid into the conduit(s) and transport same toward the pump.

22. A liquid dispensing system according to claim 19, wherein when the emanation device, in use, blows the volatile liquid from the reservoir(s) of the universal refill, the extraction means of the emanation device is provided by one or more blown air conduits that are connected at one end to a blowing means housed within the device and open at the other end to permit blown air to exit therefrom and with one or more liquid conduits that are open at one end to be in liquid communication with the volatile liquid and connected to the device at the other end.

23. A liquid dispensing system according to claim 22, wherein the blown air conduit(s) are sized to enter through one or more of the valves of the universal refill and the liquid conduit(s) are sized to extend through one or more of alternate valves in the refill and wherein both types of conduits extend into the reservoir(s) within the refill when said refill is engaged with the chassis.

24. A liquid dispensing system according to claim 22, wherein, in use, the blowing means is operable to blow air along the blown air conduit and into the reservoir(s) in order to pressurise the head space and, when required by the device, force liquid into the liquid conduit(s) and toward the device.

25. A liquid dispensing system according to claim 1, wherein, in use, the wick(s) are operable to passively uptake liquid from the reservoir(s) and transport same towards the other end of the wick(s).

26. A liquid dispensing system according to claim 1, wherein the emanation device and/or chassis is provided with securing means which are configured to engage with the universal refill to permit a secure engagement of the universal refill to the chassis.

27. A liquid dispensing system according to claim 1, wherein the universal refill and emanation devices are provided with a device-to-refill recognition system whereby the device is able to recognise the level of volatile liquid remaining in the refill and/or the type of volatile liquid in the refill and/or whether the refill is from a known source.

28. A liquid dispensing system according to claim 27, wherein the recognition system is provided by the device possessing a physical characteristic in the refill housing which interacts with a portion of the chassis and/or device.

29. A liquid dispensing system comprising a universal refill of volatile liquid and an emanation device; wherein the refill comprises:
a housing;
at least one reservoir in the housing for holding the volatile liquid;
at least two valves in the housing in communication with the reservoir, wherein each of said valves is configured to be automatically resealable when not being held open;
wherein the refill is operationally compatible with each device;
wherein the emanation device is selected from at least one of: an emanation device configured to extract the volatile liquid from the refill by pumping the liquid therefrom; an emanation device configured to extract the volatile liquid from the refill by blowing the liquid therefrom; an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom;
wherein each emanation device is provided with a chassis configured to receive and releasably retain the universal refill and wherein each device further comprises one or more liquid extraction means which are configured to extend from the device and, in use, through one or more of said valves of the universal refill;
wherein when the emanation device, in use, transports the volatile liquid from the reservoir(s) of the universal refill to the emanation device via capillary action, the extraction means of the device is provided by one or more capillary tubes that are connected at one end to the emanation device and configured at the other end to be in liquid communication with the volatile liquid to uptake same.

30. A liquid dispensing system according to claim 29, wherein the capillary tube(s) are sized to extend through one or more of the valves in the universal refill and into the reservoir(s) therewithin when the refill is engaged with the chassis.

31. A liquid dispensing system according to claim 29, wherein, in use, the capillary tube(s) are operable to passively uptake liquid from the reservoir(s) and transport same towards the other end of the tube(s).

32. A liquid dispensing system comprising a universal refill of volatile liquid and an emanation device; wherein the refill comprises: a housing; at least one reservoir in the housing for holding the volatile liquid; at least two valves in the housing in communication with the reservoir, wherein each of said valves is configured to be automatically resealable when not being held wherein the refill is operationally compatible with each device; wherein the emanation device is selected from at least one of: an emanation device configured to extract the volatile liquid from the refill by pumping the liquid therefrom; an emanation device configured to extract the volatile liquid from the refill by blowing the liquid therefrom: an emanation device configured to extract the volatile liquid from the refill by wicking the liquid therefrom; an emanation device configured to extract the volatile liquid from the refill by capillary action therefrom; an emanation device configured to extract the volatile liquid from the refill by a gravity feed therefrom; an emanation device configured to extract the volatile liquid from the refill by two or more ways selected from pumping, blowing, wicking, capillary action and/or gravity feed therefrom; wherein each emanation device is provided with a chassis configured to receive and releasably retain the universal refill and wherein each device further comprises one or more liquid extraction means which are configured to extend from the device and, in use, through one or more of said valves of the universal refill, wherein when the emanation device, in use, extracts the volatile liquid from the reservoir(s) of the universal refill toward the emanation device by a gravity feed mechanism, the extraction means of the emanation device is provided by one or more liquid conduits that are connected at one end to the device and open at the other end to be in liquid communication with the volatile liquid, wherein the liquid conduit(s) are sized to extend through one or more of the valves in the universal refill and into the reservoir(s) there within when the refill is engaged with the chassis and, wherein, in use, the liquid conduit(s) are operable to open the valve(s) to permit the volatile liquid to flow from the reservoir toward the device under the sole force of gravity.

* * * * *